United States Patent [19]

Kurtz et al.

[11] 4,324,244

[45] Apr. 13, 1982

[54] TWO-CHAMBER UNDERWATER DRAINAGE APPARATUS WITH ONEWAY OUTFLOW VALVE AND DUAL HANGAR RETAINERS

[75] Inventors: Leonard D. Kurtz, Woodmere; Robert E. Bidwell, Long Island, both of N.Y.

[73] Assignees: Robert J. Kurtz, New York, N.Y.; Alfred Kurtz, Wynnewood, Pa.

[21] Appl. No.: 120,295

[22] Filed: Feb. 11, 1980

[51] Int. Cl.³ .............................................. A61M 1/00
[52] U.S. Cl. .................................... 128/276; 248/318; 248/558
[58] Field of Search .................... 248/1, 317, 318, 558; 128/276, DIG. 24, 272, 214 D

[56] References Cited

U.S. PATENT DOCUMENTS 3,312,221 4/1967 Overment .................. 128/DIG. 24
4,015,603 4/1977 Kurtz et al. ......................... 128/276

Primary Examiner—Robert W. Michell
Assistant Examiner—J. L. Kruter
Attorney, Agent, or Firm—Larson and Taylor

[57] ABSTRACT

A two-chambered underwater drainage apparatus is provided which is adapted to be connected with the pleural cavity of a patient by means of a thorocotomy tube. The underwater seal which prevents the flow of atmospheric air from the device to the pleural cavity of the patient is formed at the lower end of the thorocotomy tube and the secretions from the body cavity form the liquid in the seal. A oneway valve is provided at the outlet from the device to prevent backflow of air from the atmosphere into the device, but, permits outflow of air from within the device when the air pressure within the device is higher than atmospheric pressure or when the device is used with a suction pump. A hanger attachment is provided which permits the device to stand on the floor or be hooked onto the bedside.

6 Claims, 4 Drawing Figures

TWO-CHAMBER UNDERWATER DRAINAGE APPARATUS WITH ONEWAY OUTFLOW VALVE AND DUAL HANGAR RETAINERS

BACKGROUND OF THE INVENTION

The invention relates to a surgical drainage system and more particularly to a device which is designed to drain fluids from a body cavity such as the plueral cavity and to maintain proper pressures within the body cavity.

It is essential for normal breathing that the space within the pleural cavity surrounding the lungs be free of liquid and be subject to a negative pressure so as to draw the lungs outwardly to fill the pleural cavity and permit proper breathing. Any invasion of the pleural cavity such as is caused by lung surgery or foreign objects which pierce the ribcage or where the patient has pleurisy, generate fluids in the pleural cavity which tend to obstruct normal breathing operations. It is necessary to provide a device which can remove these fluids from the pleural cavity and at the same time insure that the desired degree of negative pressure is maintained within the plerual cavity.

One of the basic types of apparatus which has been used for this purpose is shown, for example, in U.S. Pat. Nos. 3,363,626 and 3,363,627. This apparatus is known as an underwater drainage apparatus and provide three chambers, one chamber comprising a collection chamber for collecting the fluids drained from the pleural cavity through a thorocotomy tube, a second chamber known as an underwater seal chamber which protects the plerual cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity. However, such an apparatus required prefilling the underwater seal chamber with water and also prefilling the pressure manometer chamber to the desired level to maintain the desired degree of negativity within the pleural cavity. However, there has been a need for a drainage device which could be attached to the patient's pleural cavity and which did not require any prefilling, and which did not require a vacuum pump. For example, in emergency situations in the field where liquid may not be available for filling the underwater seal and manometer chambers or where a vacuum pump may not be available, it is necessary to provide a device which can be attached to a patient's pleural cavity to permit drainage of fluids to allow the lungs to expand.

The drainage system disclosed in U.S. Pat. No. 4,015,603 provided an apparatus which eliminated the need for a prefilled underwater seal chamber by locating the underwater seal at the lower end of the thorocotomy tube at the upper end of the drainage device. In the device shown in this prior patent, the underwater seal was formed by liquid drained from the patient's pleural cavity. However, the device disclosed in U.S. Pat. No. 4,015,603 required the use of a self-regulated vacuum pump and, in situations where such a pump was not available, the device shown in this prior art patent could not be utilized.

Furthermore, the location of the underwater seal chamber at the lower end of the thorocotomy tube as disclosed in U.S. Pat. No. 4,015,603 created a further problem in certain unusual circumstances. In case of a patient having a blockage in the bronchial tubes, such that the patient was having severe problems in getting air into the lungs, exceedingly high negativity was being created in the pleural cavity. Such high negativity caused the fluid in the underwater seal to be drawn upwardly through the thorocotomy tube and, if the degree of negativity was sufficiently high, it was possible for fluid to reenter the pleural cavity. This condition of fluid from the underwater seal chamber reentering the pleural cavity could cause infection or otherwise create problems for the patient. In addition, it was possible to entirely lose the seal provided by the underwater seal chamber during periods of high negativity in the pleural cavity. The loss of the water seal has the potential for serious damage in the event the suction becomes disconnected or the device is used as a two bottle system with the collection chamber open to atmosphere.

In U.S. Pat. No. 3,853,128 there is disclosed a positive pressure relief valve in a drainage apparatus having a conventional underwater seal and manometer chamber. The positive pressure relief valve is disposed between the underwater seal and manometer chambers and provides relief from high pressure surges within the collection chamber. The device disclosed in U.S. Pat. No. 3,853,128 must, however, be prefilled prior to use and does not function as a two chambered device which is usable without prefilling.

SUMMARY OF THE INVENTION

The present invention provides a surgical drainage system which overcomes the problems noted above with respect to prior art devices and provides an underwater drainage apparatus which does not require prefilling with water and which does not require a vacuum pump.

According to the present invention, there is provided a drainage apparatus having a collection chamber with an underwater seal chamber located at the upper end thereof adjacent the lower end of the thorocotomy tube. Thus, when the thorocotomy tube is attached to the pleural cavity, liquid drained into the thorocotomy tube passes into the underwater seal chamber and forms the underwater seal. When the seal chamber is filled, the liquid overflows into the collection chamber.

There is further provided a oneway valve which is disposed between the collection chamber and the outlet port to atmosphere. This oneway valve is designed to open to permit the escape of gases from within the collection chamber when the pressure within the chamber is higher than atmospheric but which will prevent the passage of air from the atmosphere into the collection chamber. The combination of the oneway outflow valve and the underwater seal provided by the secretions from the pleural cavity provide double protection against the possibility of a pneumothorax.

The oneway outflow valve further provides a means for preventing the backflow of fluid from the underwater seal into the pleural cavity during conditions of high negativity. The outflow valve remains closed when the pressure within the pleural cavity and drainage device is lower than atmospheric pressure and thus, limits the dead air space within the drainage device.

There are further provided means for mounting the device on the floor or, alternatively, on the side of the bed by means of hooks. In addition, the drainage device may be used with regulated suction and a positive pressure release valve is included to prevent the buildup of excessive positive pressure within the device in the event of failure of the suction pump or in the event of sudden, very high pressure surges within the pleural cavity.

Additional features and advantages of the present invention will be apparent from a consideration of the following detailed description of the preferred embodiment of the invention in connection with the accompanying drawings.

DETAILED DESCRIPTION OF THE PREFERRED EMBODIMENT

Figure 1:
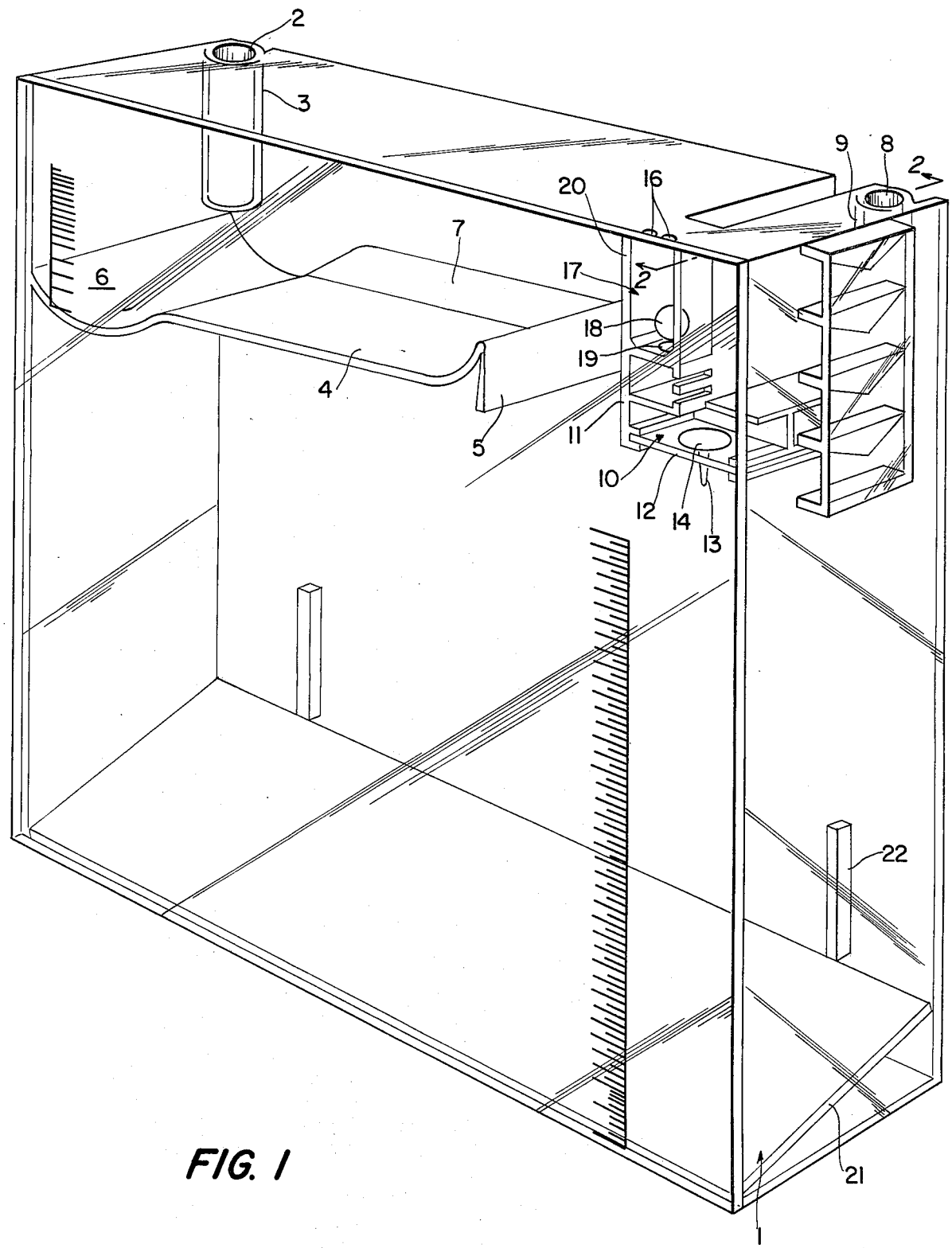
FIG. 1 is a perspective view of the two-chambered underwater drainage apparatus.

Referring now more specifically to the drawings, there is shown in FIG. 1 an underwater drainage apparatus comprising a container 1 which may be formed of a rigid transparent plastic material or the like. The container 1 is provided with an inlet 2 for attachment of a thorocotomy tube which extends into the patient's pleural cavity. It can be seen that the inlet 2 is provided with a tubular extension 3 which extends a substantial distance down into the container 1.

Within the container 1 there is provided a partition 4 which extends across the entire container and extends from one end to a lip portion 5 which is spaced from the opposite end wall of the container. The partition 4 is provided with a well shaped end portion 6 which is disposed beneath the tubular extension 3 of inlet 2. The tubular extension 3 extends downwardly into the well portion 6 of the partition member 4. The partition 4 is further provided with a sloping sidewall 7 for purposes which will be more apparent hereinafter.

Figure 2:
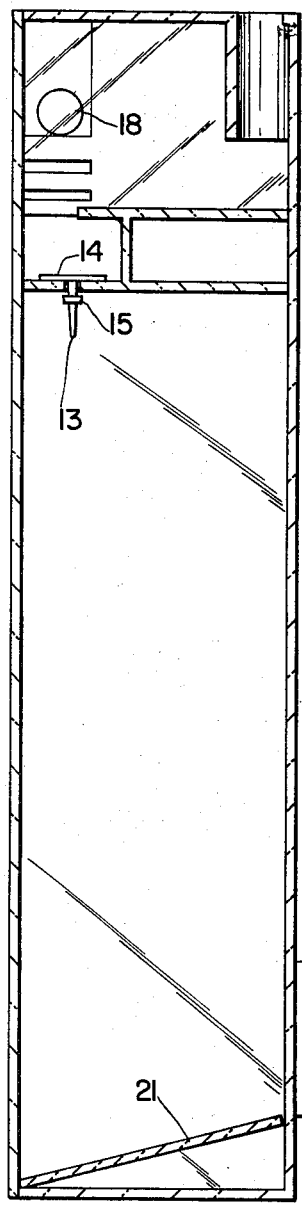
FIG. 2 is a sectional view along the line 2—2 of FIG. 1.

The drainage device is further provided with an outlet 8 which is also provided with a downwardly extending tubular extension portion 9 for receiving a flexible hose which may be attached to a regulated vacuum source. The tubular extension 9 extends into an outlet chamber 10 having a sidewall 11 and bottom wall 12 which completely closes off the outlet chamber from the remaining portion of the drainage apparatus. The bottom wall 12 of the outlet chamber is provided with an aperture and disposed within this aperture is a oneway outlet valve 13. It can be seen from FIG. 2 that this outlet valve 13 has an enlarged head 14 which extends over the openings in the bottom wall 12 of the outlet chamber. The stem of the oneway valve 13 has a stop ring 15 thereon which limits upward movement of the valve from the bottom wall. When pressures within the drainage apparatus exceed the pressures within the outlet chamber 10 the valve 13 will move upwardly so as to permit the passage of gases from the collection chamber into the outlet chamber. However, when the pressure is higher within the outlet chamber then within the collection chamber the valve 13 will remain closed with the cap 14 extending across the openings within the bottom wall 12.

There is further provided in the top wall of the apparatus openings 16. Beneath these openings is provided a positive pressure release valve 17 including a ball valve 18 which is normally disposed in a position covering an opening 19 in the bottom wall of a enclosed cage 20. The purpose of the positive pressure release valve is to provide a means for release of high positive pressure to atmosphere in the event very high pressures are reached within the collection chamber and the device is operated with a vacuum pump which is malfunctioning or unable to provide release for such high pressure. Normally, the ball 18 will remain seated over the opening 19 to maintain the valve closed and will open only in response to pressures within the collection chamber in excess of atmospheric pressure.

The drainage apparatus 1 is further provided with the sloping bottom wall 21. By utilizing a sloping bottom wall the drainage apparatus is provided with an increased sensitivity for volume measurements which are determined by a scale printed on the front face of the drainage apparatus.

Figure 3:
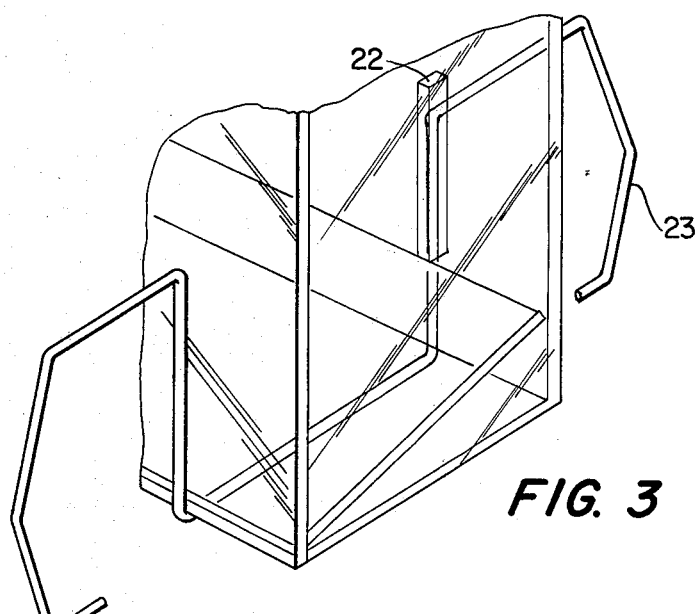
FIG. 3 is a partial perspective view of the lower portion of the drainage apparatus showing the floor stand in position.
Figure 4:
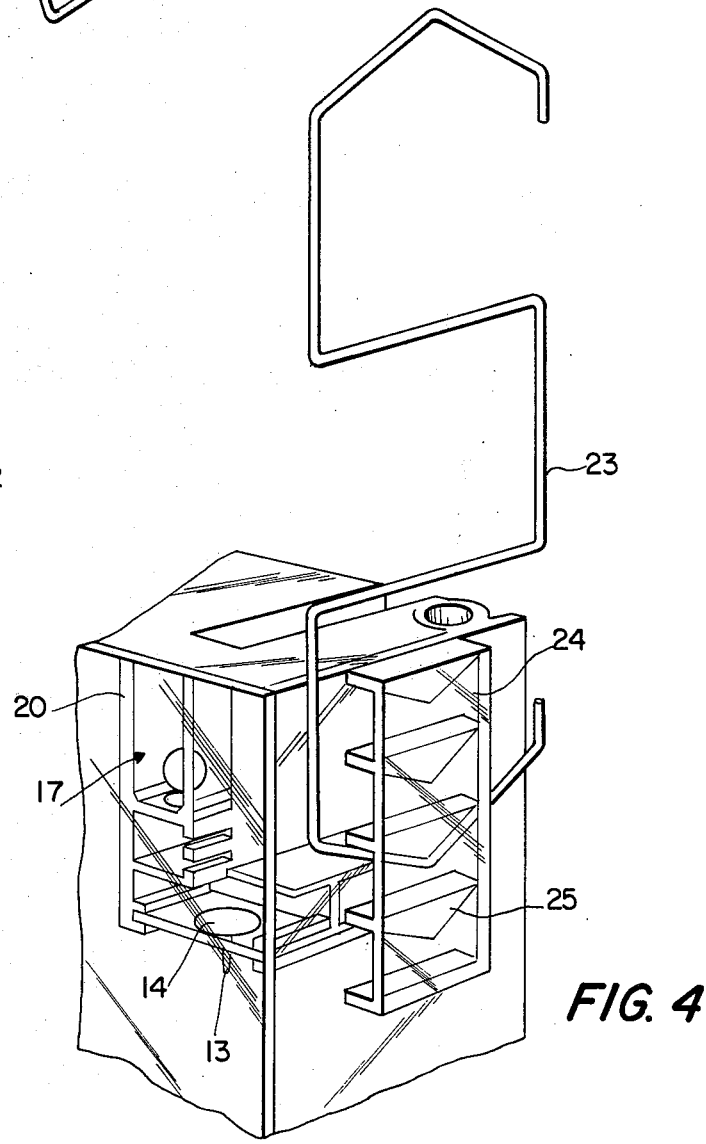
FIG. 4 is a partial perspective view of the upper portion of the underwater drainage apparatus showing the hanger in position.

The backwall of the drainage apparatus is provided with grooved guide elements 22 which are adapted to receive hanger elements 23 which are shaped as shown in FIG. 3 so as to provide a floor stand for the drainage apparatus when the apparatus must be supported on the floor. There are further provided hanger elements 24 having a series of supporting brackets 25 fixed to each end of the drainage apparatus. In the event that the apparatus is to be supported from a bedrail, the brackets 23 are supported as shown in FIG. 4.

When the drainage apparatus is to be used it is unnecessary to prefill the fluid seal. The thorocotomy tube is connected to the inlet 2 and the oneway outlet valve 13 protects the patient from admission of atmospheric air. The secretions from the pleural cavity initially fill the well 6 of the fluid seal chamber to provide an underwater seal at the lower end of tubular extension 3 of the thorocotomy tube. When the liquid fills the fluid seal chamber formed by the partition 4 to a level of the upper edge of lip 5, further secretions overflow the lip 5 and fall into the collection chamber. Initially, accurate measurements of the fluid secretions can be measured by reason of the sloping bottom wall 21 of the drainage apparatus. This is particularly helpful in connection with pediatric cases. The drainage apparatus disclosed may be used with or without regulated suction. In the event suction is to be used, the hose from the regulated suction source is attached to outlet 8 and the desired degree of negativity may be maintained within the collection chamber and pleural cavity. When operated with suction, additional protection is provided against the possible buildup of positive pressure within the chamber and pleural cavity by the positive pressure release valve 17 which will open in the event of sudden high pressure surges within the collection chamber.

In the use of drainage devices wherein the underwater seal is formed directly at the end of the thorocotomy tube by the secretions from the patient's pleural cavity, it is important that the drainage apparatus be so constructed that excessive negativity within the pleural cavity such as might be caused by blockage in the bronchial tubes or the like, cannot cause the fluid within the underwater seal to rise within the thorocotomy tube and pass back into the pleural cavity. In prior art two-chambered systems such as disclosed in prior U.S. Pat. No. 4,015,603 when open to atmospheric pressure a rise of fluid within the thorocotomy tube of 18 inches could be produced by a negative pressure of 45 centimeters of water whereas the present apparatus which incorporates a oneway outflow valve a negative pressure of 62.8 centimeters of water is required to produce such a rise of liquid in the thorocotomy tube. If the thorocotomy tube is at least thirty inches long with the present apparatus a negativity of 100.6 centimeters of water would be required to cause the fluid within the underwater seal to reenter the pleural cavity. Thus, the presently disclosed apparatus provides substantial protection against the reentry into the pleural cavity of secretions within the underwater seal chamber. This additional protection is due to the oneway outflow valve which is disposed in series with the underwater seal and provided additional protection against the possibility of pneumothorax caused by atmospheric air reaching the pleural cavity.

Obviously many modifications and variations of the present invention are possible in light of the above teachings.

What is claimed as new and is desired to be secured by Letters Patent is:

1. A drainage apparatus comprising a housing, a collection chamber formed in said housing for receiving fluids from the body of a patient, an inlet at the upper end of said housing, a partition extending across a portion of the housing to form an underwater seal chamber beneath said inlet, a tubular extension connected to said inlet and projecting downwardly into said underwater seal chamber whereby fluids from the body of a patient are collected in the underwater seal chamber and provide a fluid seal with the lower end of the tubular extension, an outlet to atmosphere disposed in said housing, oneway valve means disposed in said housing between said outlet and the interior of said collection chamber for permitting the outflow of gases from said collection chamber through said outlet and for preventing the reverse flow of such gases, a first hanger retaining means mounted on a side wall of said housing, a second hanger retaining means mounted on an end wall of said housing and hanger means for selectively engaging one of said hanger retainer means for supporting said drainage apparatus from the floor and for alternatively engaging the other of said hanger retainer means for supporting the drainage apparatus on the side of the bed.

2. A drainage apparatus according to claim 1 wherein said oneway valve means comprises an outlet chamber disposed within said collection chamber beneath said outlet and said oneway valve disposed in a wall of said outlet chamber.

3. A drainage apparatus according to claim 2 and further including a positive pressure release valve and a second outlet to atmosphere disposed within said outlet chamber.

4. A drainage apparatus according to claim 2 wherein the underwater seal and said oneway valve are disposed in series in the gas passageway between said inlet and said outlet.

5. A drainage apparatus according to claim 1 and further including a sloping bottom wall for said collection chamber to provide increased sensitivity for volume measurements.

6. A drainage apparatus according to claim 1 wherein said hanger means engages the side wall retaining means when the apparatus is to be floor supported and engages the end wall retaining means when the apparatus is to be bed supported.

* * * * *